United States Patent
Kasai et al.

(10) Patent No.: US 7,763,654 B2
(45) Date of Patent: *Jul. 27, 2010

(54) CRYSTAL POLYMORPH OF HYDROXYNOREPHEDRIN DERIVATIVE HYDROCHLORIDE

(75) Inventors: Kiyoshi Kasai, Joetsu (JP); Michio Toda, Matsumoto (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 135 days.

This patent is subject to a terminal disclaimer.

(21) Appl. No.: 11/912,407

(22) PCT Filed: Apr. 24, 2006

(86) PCT No.: PCT/JP2006/308592

§ 371 (c)(1),
(2), (4) Date: Oct. 24, 2007

(87) PCT Pub. No.: WO2006/123517

PCT Pub. Date: Nov. 23, 2006

(65) Prior Publication Data

US 2009/0069421 A1 Mar. 12, 2009

(30) Foreign Application Priority Data

Apr. 26, 2005 (JP) ............................. 2005-128733

(51) Int. Cl.
*A61K 31/24* (2006.01)
*C07C 229/00* (2006.01)
(52) U.S. Cl. ........................................ 514/539; 560/42
(58) Field of Classification Search ...................... None
See application file for complete search history.

(56) References Cited

U.S. PATENT DOCUMENTS

2004/0242686 A1 12/2004 Isawa et al.

FOREIGN PATENT DOCUMENTS

WO 03024916 A1 3/2003

*Primary Examiner*—Paul A Zucker
(74) *Attorney, Agent, or Firm*—Sughrue Mion, PLLC

(57) ABSTRACT

The present invention provides a novel crystal polymorph of ethyl (−)-2-[4-[2-[[1S,2R]-2-hydroxy-2-(4-hydroxyphenyl)-1-methylethyl]amino]ethyl]-2,5-dimethylphenoxyacetate hydrochloride which can be determined by characteristic diffraction peaks of the powder X-ray diffraction or the like, and obtained from ethyl (−)-2-[4-[2-[[1S,2R]-2-hydroxy-2-(4-hydroxyphenyl)-1-methylethyl]amino]ethyl]-2,5-dimethylphenoxyacetate by a specific method.

3 Claims, 12 Drawing Sheets

CRYSTAL POLYMORPH OF HYDROXYNOREPHEDRIN DERIVATIVE HYDROCHLORIDE

CROSS REFERENCE TO RELATED APPLICATIONS

This application is a National Stage of International Application No. PCT/JP2006/308592 filed on Apr. 24, 2006, claiming priority based on Japanese Patent Application No. 2005-128733, filed Apr. 26, 2005, the contents of all of which are incorporated herein by reference in their entirely.

TECHNICAL FIELD

The present invention relates to a novel crystal polymorph of ethyl (−)-2-[4-[2-[[1S,2R]-2-hydroxy-2-(4-hydroxyphenyl)-1-methylethyl]amino]ethyl]-2,5-dimethylphenoxyacetate hydrochloride represented by the following formula (I):

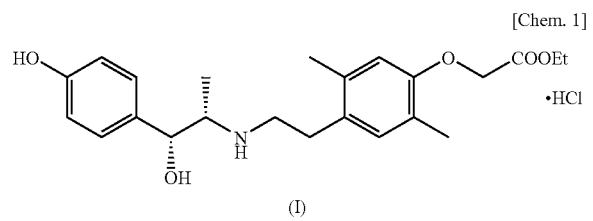

(I)

which has a $\beta_3$-adrenaline receptor stimulating effect and is useful as an agent for treating pollakiuria or urinary incontinence.

BACKGROUND ART

A hydroxynorephedrine derivative represented by the following formula (II):

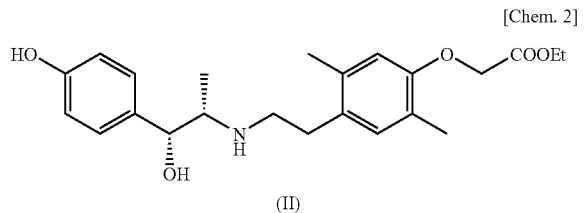

(II)

has been reported as having an excellent $\beta_3$-adrenaline receptor stimulating effect and being a useful compound as a therapeutic agent for pollakiuria or urinary incontinence (see Patent reference 1).

Heretofore, as a crystalline hydroxynorephedrine derivative hydrochloride represented by the above formula (I), crystalline forms A and B have been reported (see Patent reference 2).

Particularly, crystals represented by the above formula (I) wherein the diffraction pattern by the powder X-ray diffractometry shows characteristic peaks at diffraction angles (2θ) of 8.9, 10.2, 12.9, 14.2, 15.6, 18.4 and 20.6 (crystalline form A) and the diffraction pattern by the powder X-ray diffractometry shows characteristic peaks at diffraction angles (2θ) of 7.3, 10.1, 12.2, 14.6, 15.9, 16.0, 18.7 and 21.8 (crystalline form B) have been reported. However, from the diffraction chart by the powder X-ray diffractometry, crystals of the hydroxynorephedrine derivative hydrochloride of the present invention are novel crystal polymorphs which are different from these crystals.

Patent reference 1: International Publication No. WO00/02846 pamphlet

Patent reference 2: International Publication No. WO03/024916 pamphlet

DISCLOSURE OF THE INVENTION

Objects to be Solved by the Invention

Usually, in a compound which has crystal polymorphs, each crystal polymorph has a different property in various ways, and even if it is the same compound, it may show a different interaction effect. Especially, in case of medicines, a stable supply of the compound having the constant crystal polymorph is required so that constant interaction effects can be always expected. Therefore, it is desired earnestly to establish a stably manufacturing method to get a compound having the constant crystal polymorph.

In addition, newly finding a new crystal polymorph of a compound that is useful as a medicament can provide a new opportunity to improve the performance characteristic of the medicine. For example, this makes it possible to widen materials for a pharmaceutical researcher to design the dosage form of the medicine having a desired characteristic.

Therefore, the object of the present invention is to provide a novel crystal polymorph of the hydroxynorephedrine derivative hydrochloride represented by the above formula (I) and a manufacturing method therefor.

Means of Solving the Problems

In order to solve the aforementioned problems, as a result the present inventors have studied earnestly on crystalline hydroxynorephedrine derivatives hydrochloride represented by the above formula (I), the present inventors acquired the knowledge that a novel crystal polymorph can be prepared with constant quality according to using the specific processes that the inventors found as described below as the situation demands, thereby forming the bases of the present invention.

That is, the present invention relates to a crystal represented by the following formula (I):

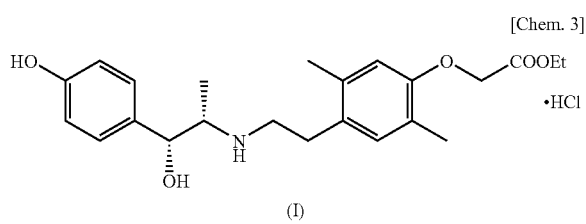

(I)

wherein the diffraction pattern by the powder X-ray diffractometry has characteristic peaks at diffraction angles (2θ) of 9.0, 13.6, 18.7, 20.6 and 24.8 (crystalline form C).

Crystalline form C of the compound represented by the above formula (I) can be prepared in the following way.

Crystalline Form C

The hydrochloride salt of the above compound (II) which can be prepared by the method described in Example 1 of Patent reference 2 is dissolved by heating in 2 to 3 times the amount of methanol. After to this reaction mixture is added 15 to 25 times the amount of ethyl acetate or toluene and it is dissolved by heating, optionally, 10 to 20% of the solvate is removed under normal pressure. The crystals which are precipitated under ice-cooling to at room temperature are collected by filtration to obtain crystalline form C.

In addition, by the following manufacturing methods, crystal polymorphs (crystalline form D and crystalline form E) which are different from crystalline form C can be prepared. Herewith, each of crystalline forms C, D and E can be prepared with constant quality according to using each specific process which the inventors found.

Crystalline Form D

Crystalline form D can be prepared by using as a material ethyl (−)-2-[4-[2-[[(1S,2R]-2-hydroxy-2-(4-hydroxyphenyl)-1-methyl-ethyl]amino]ethyl]-2,5-dimethylphenoxyacetate hydrochloride ¼ hydrate which is prepared by the following method.

That is, to ethyl (−)-2-[4-[2-[[(1S,2R)-2-hydroxy-2-(4-hydroxyphenyl)-1-methylethyl]amino]ethyl]-2,5-dimethylphenoxy]acetate which is prepared by the method described in Patent reference 1 is added 2 to 5 times the amount of toluene to dissolve. About 1 equivalent of 30 weight % hydrogen chloride in ethanol is added to the mixture under ice-cooling, and the reaction mixture is stirred for 1 to 3 hours at 20 to 30° C. The precipitated crystals are collected and dried under reduced pressure at about 60° C. By storing the obtained crystals under an atmosphere of a temperature between 20 to 30° C. and a relative humidity between 50 to 70% for one night or more, ethyl (−)-2-[4-[2-[[(1S,2R)-2-hydroxy-2-(4-hydroxyphenyl)-1-methylethyl]amino]ethyl]-2,5-dimethylphenoxy]-acetate hydrochloride ¼ hydrate can be prepared. By removing the water of crystallization under a specific condition of heating for 20 to 40 minutes at 60 to 70° C., crystalline form D can be prepared.

The obtained crystal shows the diffraction pattern by the powder X-ray diffractometry having characteristic peaks at diffraction angles (2θ) of 6.5, 11.8, 13.3, 15.1, 17.9 and 20.1.

Crystalline Form E

Crystalline form E can be obtained by changing the condition when the water of crystallization is removed from ethyl (−)-2-[4-[2-[[(1S,2R)-2-hydroxy-2-(4-hydroxyphenyl)-1-methylethyl]-amino]ethyl]-2,5-dimethylphenoxy]acetate hydrochloride ¼ hydrate which is prepared by the above-mentioned method. That is, crystalline form E can be obtained under the condition of heating ethyl (−)-2-[4-[2-[[(1S,2R)-2-hydroxy-2-(4-hydroxyphenyl)-1-methyl-ethyl]amino]ethyl]-2,5-dimethylphenoxy]acetate hydrochloride ¼ hydrate which is prepared by the above method at 110 to 130° C. for 10 to 20 minutes.

As mentioned above, it is important for obtaining crystalline forms D and E to remove the water of crystallization under each specific condition: heating the hydrate prepared by the above-mentioned method at from 60 to 70° C. for 20 to 40 minutes (method 1) or at from 110 to 130° C. for 10 to 20 minutes (method 2), and crystalline forms D and E can be first prepared by conducting each of these specific handlings respectively. Therefore, for example, crystalline forms D and E can not be prepared only by the manufacturing method described in Example 1 of Patent reference 2.

Crystalline forms C, D and E which can be obtained by the above methods can be identified by the following diffraction peaks as shown in the powder X-ray diffraction charts of FIGS. 1, 3 and 4.

That is,
(1) Crystalline form C has characteristic peaks at diffraction angles (2θ) of 9.0, 13.6, 18.7, 20.6 and 24.8 degrees as shown in FIG. 1.
(2) Crystalline form D has characteristic peaks at diffraction angles (2θ) of 6.5, 11.8, 13.3, 15.1, 17.9 and 20.1 degrees as shown in FIG. 3.
(3) Crystalline form E has characteristic peaks at diffraction angles (2θ) of 6.4, 9.8, 12.0, 15.1, 19.9 and 21.3 degrees as shown in FIG. 4.

In addition, each crystal polymorph can also be discriminated by thermogravimetry-differential thermal analysis (TG/DTA) or solid state $C^{13}$-NMR spectrum. Each data of the thermogravimetry-differential thermal analysis (TG/DTA) are shown in FIGS. 5 to 8, and the solid state $C^{13}$-NMR spectrum are shown in FIGS. 9 to 12.

Crystalline form C which can be obtained by the above method has a property that polymorphic transformation does not occur during the storage at a high temperature (60° C. and 1 week) and its chemical stability is excellent. Moreover, since polymorphic transformation is not observed at a higher temperature (for example, 140° C.), the crystal is stable against an exothermic heat which is caused by drug formulation process (for example, a heat produced by making tablet), and therefore, a drug formulation can be conducted with the crystalline form kept constant.

The crystal polymorph of the present invention exhibits an excellent $\beta_3$-adrenoceptor stimulating effect and relaxes bladder detrusor muscle and increases the volume of bladder. Therefore, crystalline form C can be used for the treatment of dysuria such as pollakiuria or urinary incontinence in nervous pollakuria, neurogenic bladder dysfunction, nocturia, unstable bladder, cystospasm, chronic or acute cystitis, prostatic hypertrophy or the like, or idiopathic pollakiuria, idiopathic urinary incontinence or the like.

The crystal polymorph related to the present invention can be used, if required, in combination with another medicament for the treatment of dysuria. Examples of such a medicament for the treatment dysuria include anticholinergic agents such as oxybutynin hydrochloride, propiverine hydrochloride, tolterodine, darifenacin, fesoterodine, trospium chloride, KRP-197, YM-905 and the like; smooth muscle relaxants such as flavoxate hydrochloride and the like; $\beta_2$-adrenoceptor agonists such as clenbuterol hydrochloride, formoterol fumarate and the like; $\alpha_1$-adrenoceptor agonists such as midodrine hydrochloride, R-450, GW-515524, ABT-866 and the like; estrogen preparations such as conjugated estrogen, estriol, estradiol and the like; central nervous system agents such as antiepileptic agents, antidepressants and the like such as imipramine, reserpine, diazepam, carbazapam and the like; neurokinin receptor antagonists such as TAK-637, SB-223956, AZD-5106 and the like; potassium channel openers such as capsaicin, resiniferatoxin and the like; vasopressin 2 receptor agonists such as desmopressin, OPC-51803, WAY-141608 and the like; a1-adrenoceptor antagonists such as tamsulosin, urapidil, naftopidil, silodosin, terazosin, prazosin, alfuzosin, fiduxosin, AIO-8507L and the like; serotonin receptor antagonists such as REC-15-3079 and the like; dopamine receptor agonists such as L-dopa and the like, or dopamine receptor antagonists; antiallergic agents such as histamine receptor antagonists such as sulplatast tosilate, norastemizole and the like; NO synthase inhibitors such as nitroflurbiprofen and the like.

The pharmaceutical compositions related to the present invention can be prepared, for example, by suitably admixing or by diluting and dissolving crystalline form C with appropriate pharmaceutical additives such as excipients, disintegrators, binders, lubricants, diluents, buffers, isotonicities, antiseptics, moistening agents, emulsifiers, stabilizing agents, dissolving aids and the like by pharmaceutically well-known method depending on the formulation.

In case of using a pharmaceutical composition comprising as an active ingredient the crystal polymorph of the present invention in the practical treatment, various dosage forms can be used depending upon their usages. As the dosage forms, for example, powders, granules, fine granules, dry syrups, tablets, capsules, injections, solutions, ointments, suppositories, poultices or the like can be illustrated, and they are orally or parenterally administered.

In case of using a pharmaceutical composition of the present invention in the practical treatment, the dosage of crystalline form C that is an active ingredient is appropriately decided depending on the age, sex, body weight and degree of symptoms and treatment of each patient, which is approximately within the range of from 0.01 to 100 mg per day per adult human in the case of oral administration and approximately within the range of from 0.003 to 30 mg per day per adult human in the case of parenteral administration, and the daily dose can be divided into one to several doses per day and administered suitably.

In case of uses of the crystal polymorph related to the present invention in combination with another medicament for the treatment of dysuria, pharmaceutical compositions can be formulated by admixing separately each of active ingredients, or admixing concurrently both of active ingredients, with pharmaceutically acceptable additives such as excipients, disintegrators, binders, lubricants, diluents, buffers, isotonicities, antiseptics, moistening agents, emulsifiers, stabilizing agents, dissolving aids and the like, and orally or pareterally administered. In case that pharmaceutical compositions are separately formulated, the compositions may be mixed together with an appropriate diluent and administered simultaneously. Alternatively, separately formulated pharmaceutical compositions may be administered separately, concurrently or at different intervals.

Effects of the Invention

This time, since crystalline forms C, D and E newly find, they can provide a new opportunity to improve the performance characteristic of the medicine. For example, this leads to making it possible to widen the materials for pharmaceutical researcher to designing the dosage form of the medicine having a desired characteristic. Particularly, crystalline form C has an excellent storage stability wherein it has a property that polymorphic transformation does not be caused during storage under a high temperature (60° C. and 1 week) and chemical stability is excellent. Moreover since polymorphic transformation does not be observed under more high temperature (for example, 140° C.), a drug formulation can be conducted by maintaining the crystalline form constantly against an exothermic heat which is caused by drug formulation process (for example, heat produced by making tablet).

BEST MODE TO PUT THE INVENTION TO PRACTICE

Figure 1:
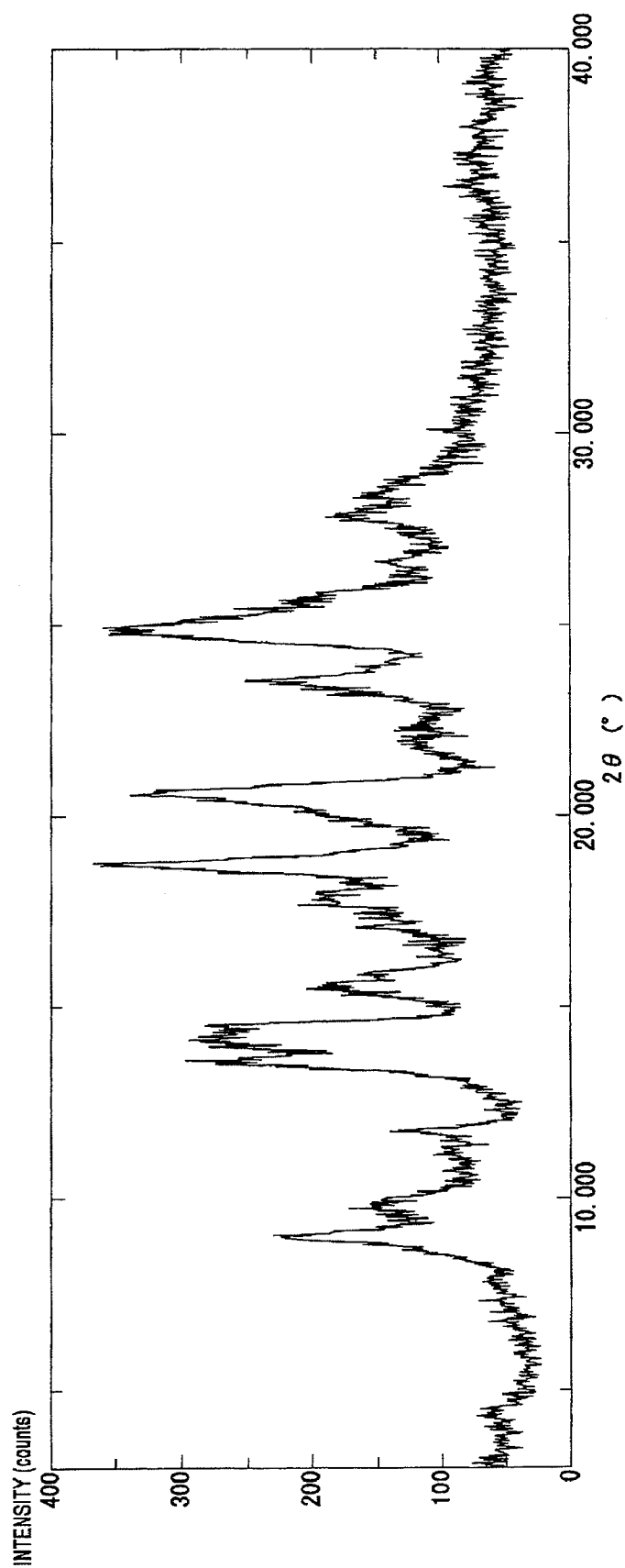
FIG. 1 shows powder X-ray diffraction diagram of crystalline form C obtained in Example 1. The axis of ordinate shows the intensity of X-rays, and the axis of abscissa shows the angle of the diffraction (2θ).

The present invention is further illustrated in more detail byway of the following Test Examples. However, the present invention is not limited thereto.

The powder X-ray diffraction data of each crystal polymorph were measured by X-ray diffractometer RINT 2100 ultima+manufactured by Rigaku Denki Corporation (measuring conditions; CuK α rays, 40 kV in X-ray tube voltage, 40 mA in X-ray tube current). The 2θ value of diffraction pattern by the powder X-ray diffractometry may deviate in some cases by a factor of about 0.5° depending on the sample conditions and measuring conditions. In addition, due to the properties of data, a total diffraction pattern of the powder X-ray diffractometry is important for the identification of crystals. The TG/DTA measurements of each crystal polymorph were conducted by thermogravimetry analyzer (TG/DTA) ThermoPlus 2 series TG8120 manufactured by Rigaku Denki Corporation (measuring conditions; temperature rising rate 10° C./minutes, samplepan (Al), reference ($Al_2O_3$), under a nitrogen atmosphere). Melting points of each crystal were searched from differential thermal analysis (DTA) endothermic peak (extrapolation). The solid state $C^{13}$-NMR spectrums of each crystal polymorph were measured by AVANCE/DRX500 manufactured by Bruker (measuring conditions; accumulated counts 512 times, contact time 3 msec, repeated time 5 sec, probe 4 mm MAS, observed frequency 125.77 Mhz, spinning rate 10000 Hz).

EXAMPLES

Example 1

Figure 5:
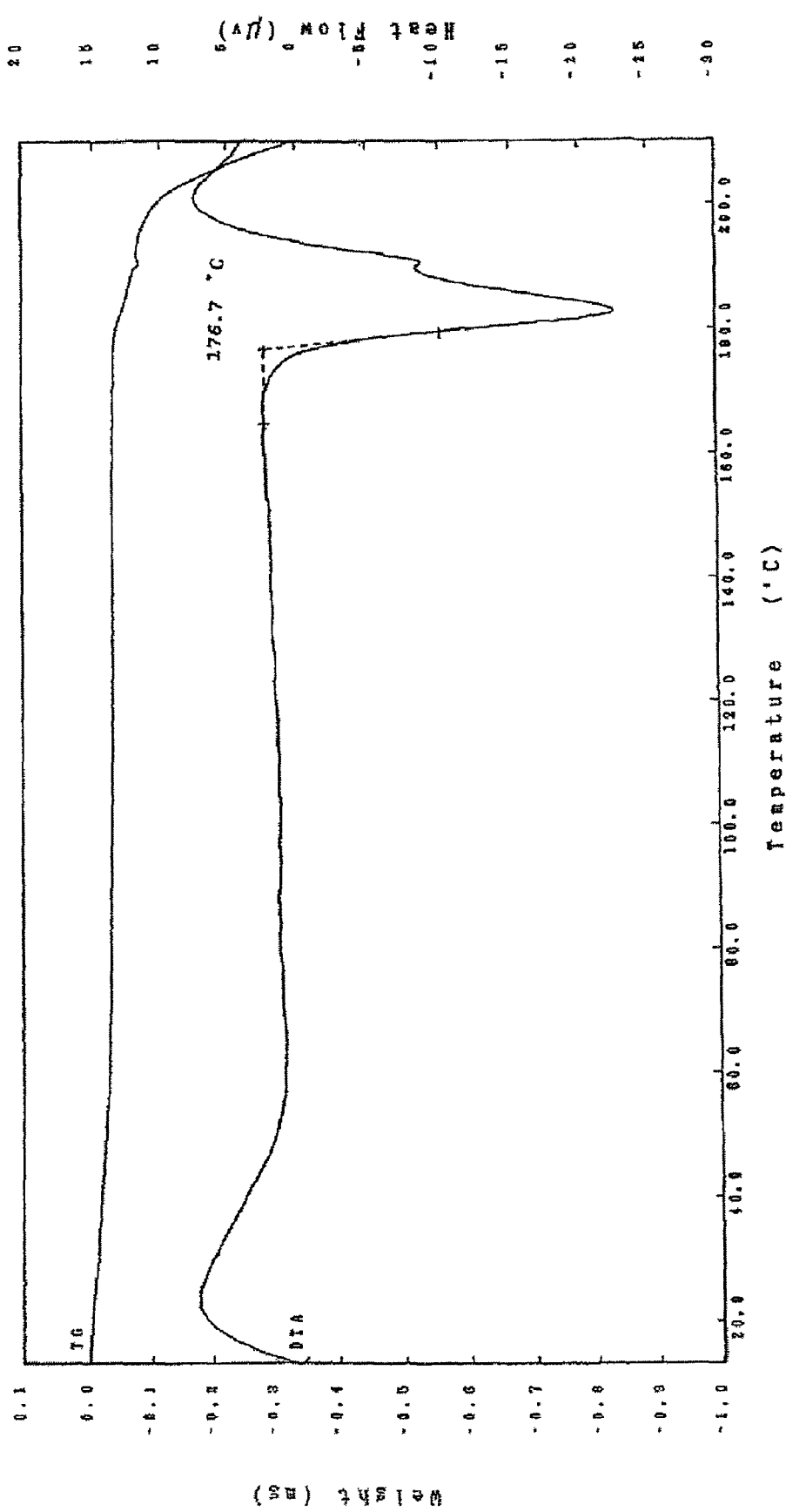
FIG. 5 shows TG/DTA data of crystalline form C obtained in Example 1 shown by the TG/DTA curves. The axis of ordinate shows the heat flow and weight, and the axis of abscissa shows the temperature.
Figure 9:
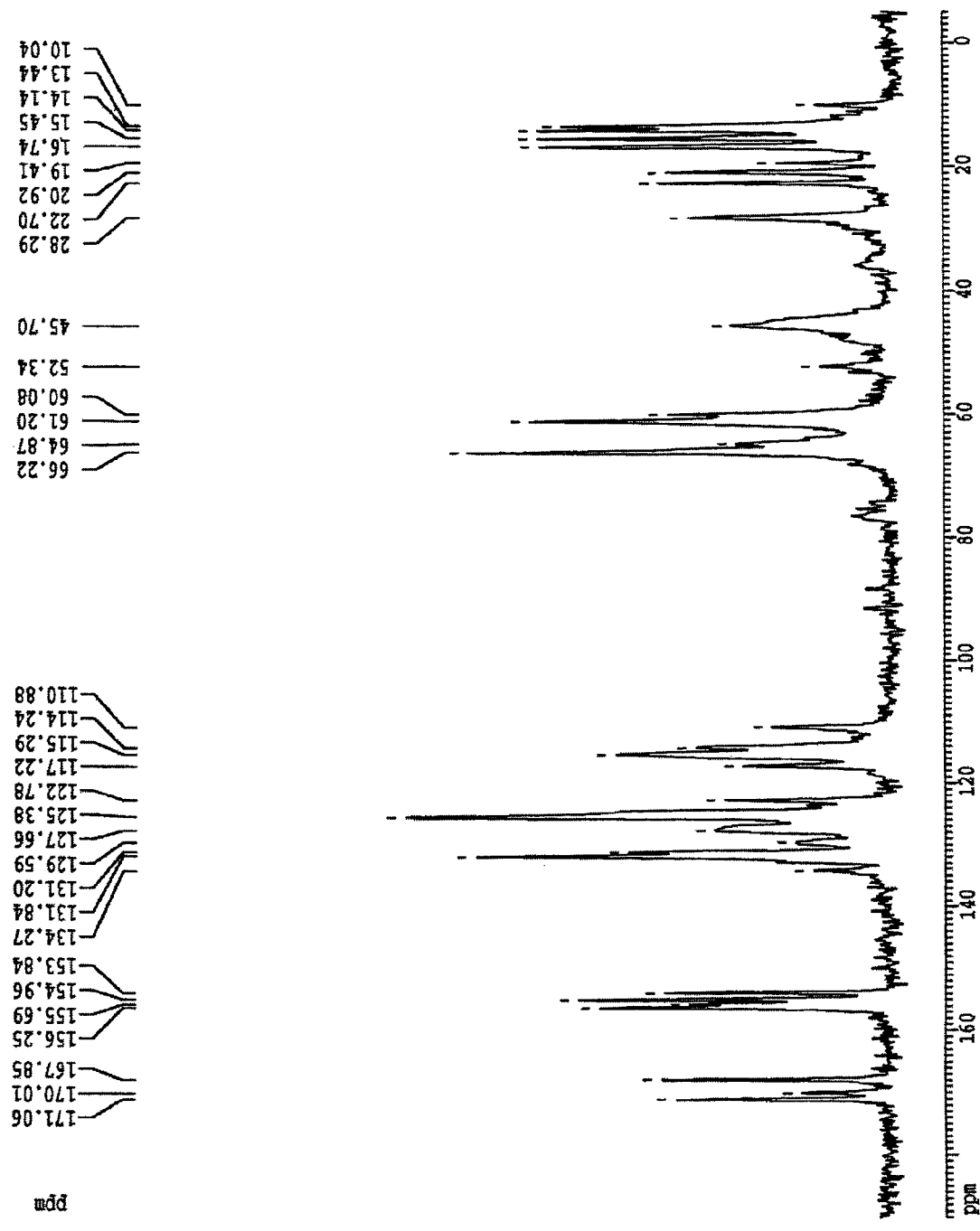
FIG. 9 shows solid state $C^{13}$-NMR spectrum of crystalline form C obtained in Example 1, the axis of abscissa shows the chemical shifts (ppm).

Crystalline form C of ethyl (−)-2-[4-[2-[[(1S,2R)-2-hydroxy-2-(4-hydroxyphenyl)-1-methylethyl]amino]ethyl]-2,5-dimethylphenoxy]-acetate hydrochloride Ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride (10 g) represented by the above formula (I) which was prepared by the method described in Example 1 of Patent reference 2 was dissolved in methanol (20 mL) by heating. Ethyl acetate (200 mL) was added to the solution and 38 mL of the solvent was removed under normal pressure by heating. After the mixture was cooled at room temperature, the precipitated crystals were collected by filtration and dried at room temperature in vacuo to give 9.2 g of crystals. The obtained crystals were measured by the powder X-ray diffraction analysis, and the result is shown in FIG. 1. In addition, TG/DTA analysis (the result is shown in FIG. 5) was conducted and solid state $^{13}$C-NMR spectrum (the result is shown in FIG. 9) was also measured.

Diffraction angles (2°): 9.0, 13.6, 18.7, 20.6 and 24.8

Melting point: 174 to 177° C.

Reference Example 1

Figure 2:
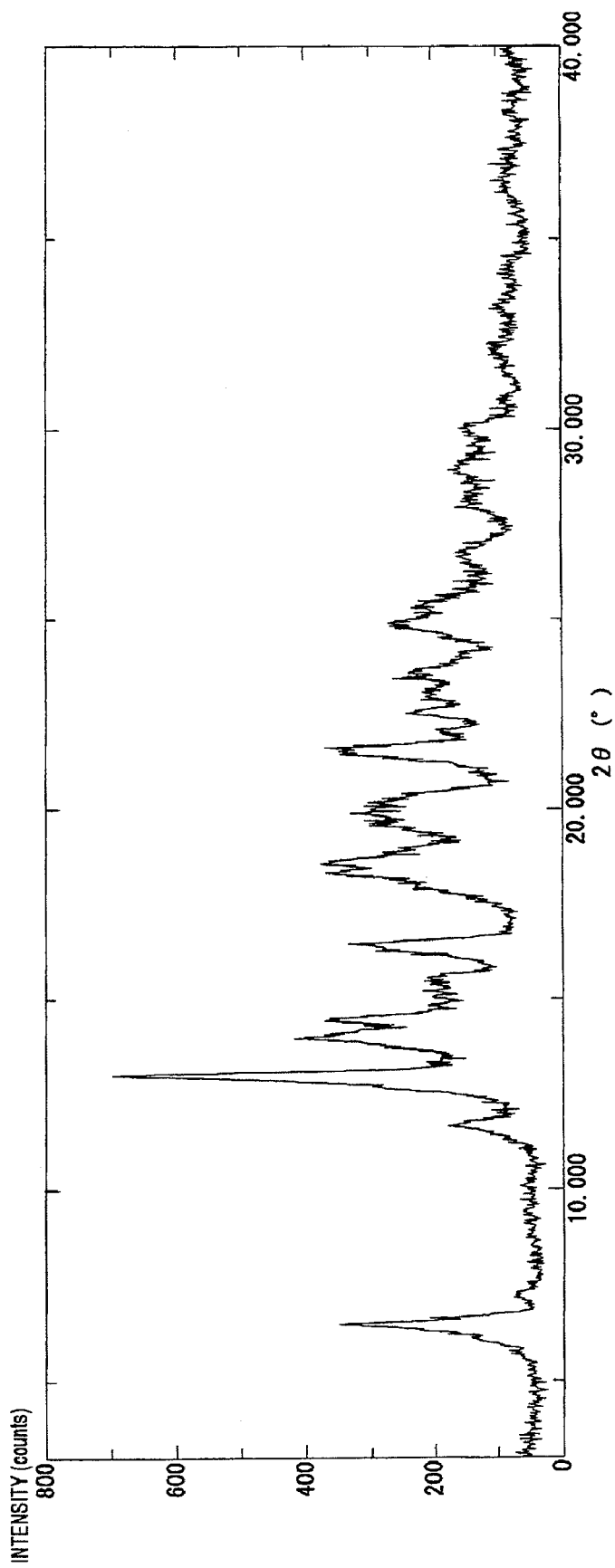
FIG. 2 shows powder X-ray diffraction diagram of a compound obtained in Reference example 1. The axis of ordinate shows the intensity of X-rays, and the axis of abscissa shows the angle of the diffraction (2θ).
Figure 6:
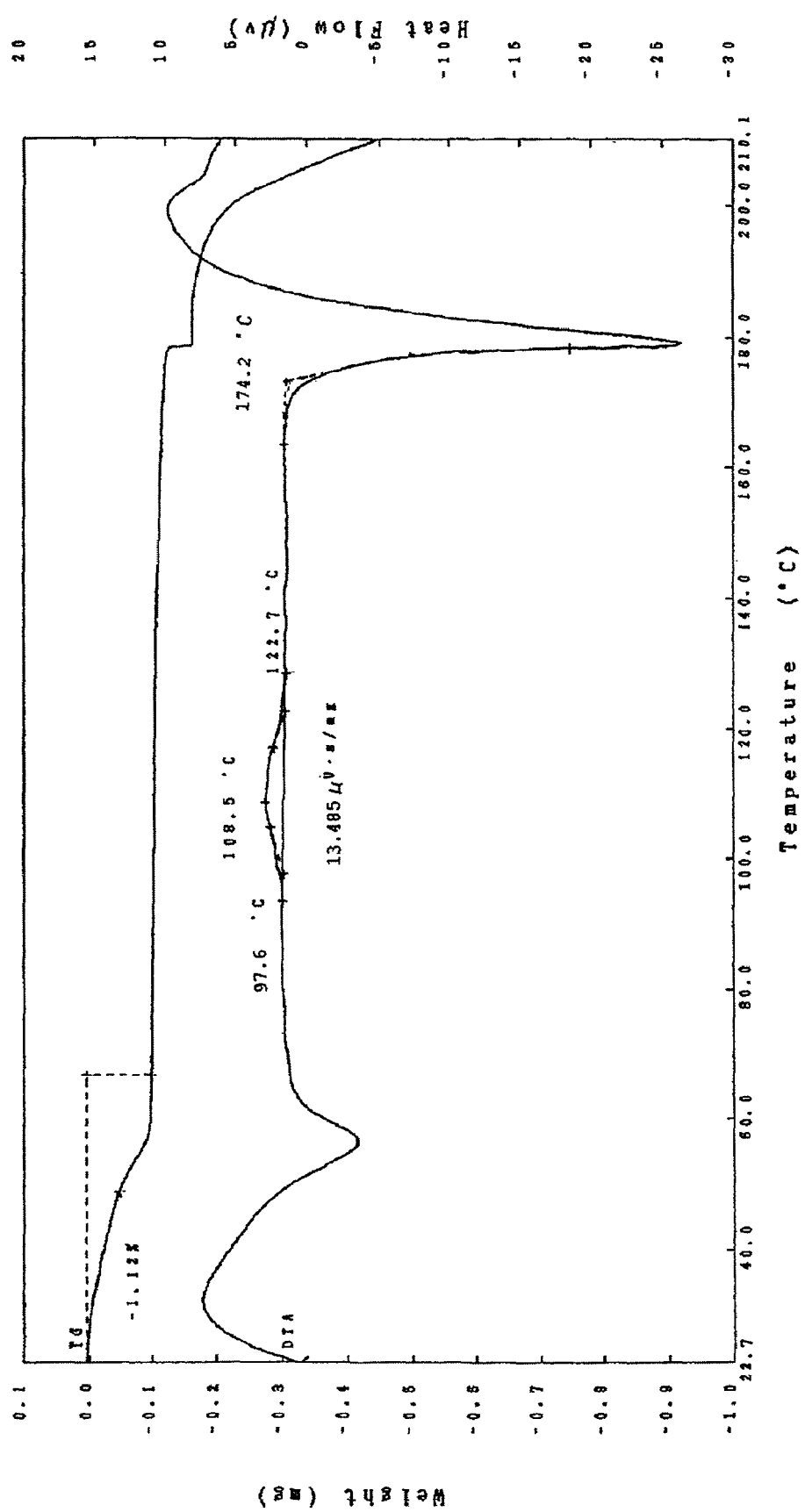
FIG. 6 shows TG/DTA data of a compound obtained in Reference example 1 shown by the TG/DTA curves. The axis of ordinate shows the heat flow and weight, and the axis of abscissa shows the temperature.
Figure 10:
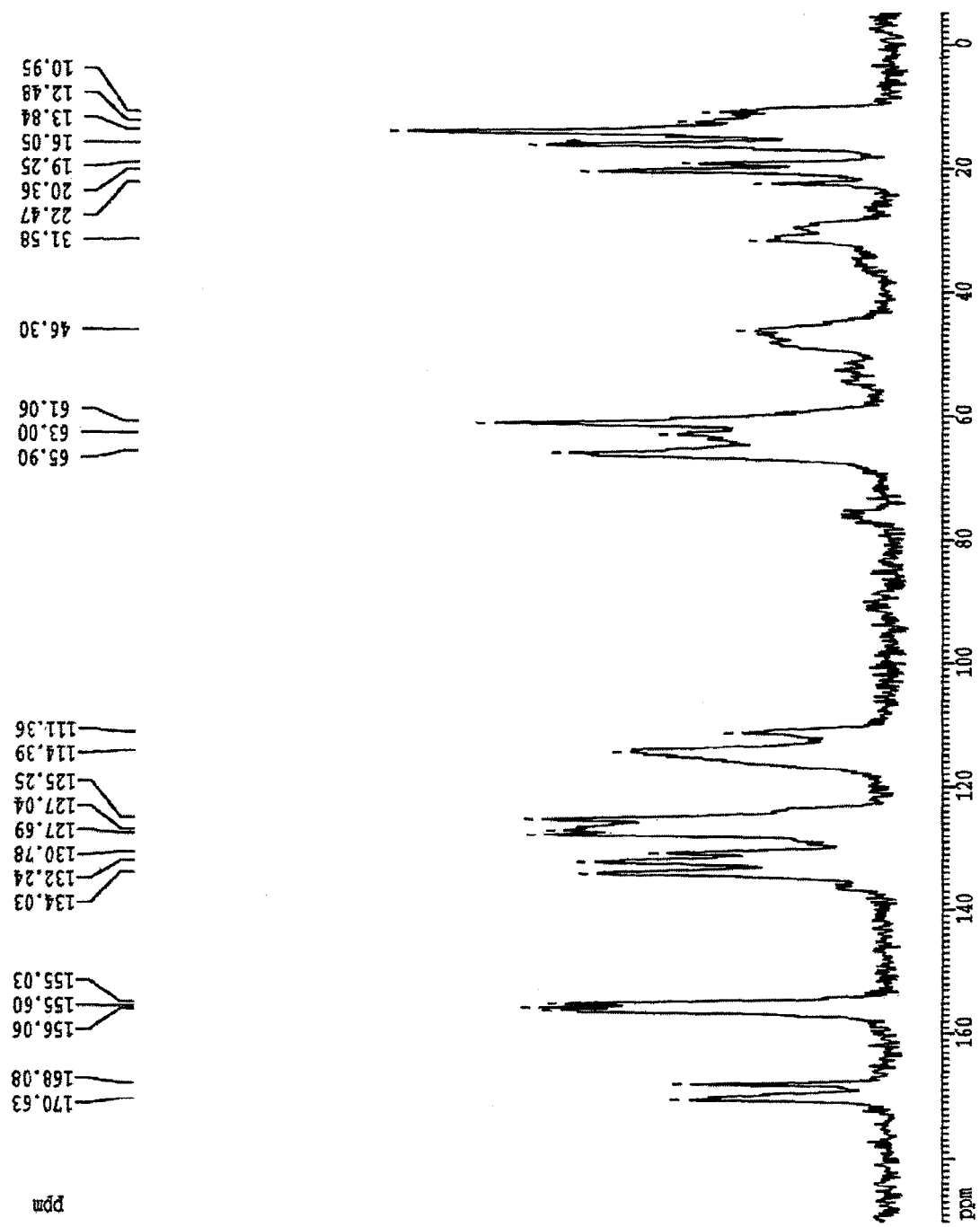
FIG. 10 shows solid state $C^{13}$-NMR spectrum of a compound obtained in Reference example 1, the axis of abscissa shows the chemical shifts (ppm).

Ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride ¼ hydrate A mixture of ethyl 2-[4-(2-bromoethyl)-2,5-dimethyl-phenoxy]acetate (11.3 g), (1R,2S)-p-hydroxynorephedrine (5.0 g), diisopropylamine (4.54 g) and N,N-dimethylformamide (28 g) was stirred at 100° C. for 2 hrs under a nitrogen atmosphere. After cooling the reaction mixture to room temperature, ethyl acetate (90 g) and water (38 g) were added to the reaction mixture. The organic layer was separated, and the aqueous layer was extracted with ethyl acetate (45 g). The combined organic layers were washed with water and brine successively, and dried over anhydrous sodium sulfate. After the drying agent was separated by filtration, the solvent was removed under reduced pressure. Furthermore, the reaction mixture was heated to remove the solvent by azeotropy with toluene (20 g), and toluene (28.4 g) was added to the residue. To the resultant solution was added 30 weight % hydrogen chloride solution in ethanol (3.06 g) under ice cooling, and the resulting mixture was stirred at 20° C. for 2 hrs. The precipitated crystals were collected by filtration, dried at 60° C. for 4 hrs in vacuo and allowed to stand overnight at 25° C. and at 60% relative humidity to give ethyl (−)-2-[4-[2-[[(1S,2R)-2-hydroxy-2-(4-hydroxyphenyl)-1-methylethyl]amino]ethyl]-2,5-dimethyl-phenoxy]acetate hydrochloride ¼ hydrate (7.36 g). The obtained crystals were measured by the powder X-ray diffraction analysis. The result is shown in FIG. 2. In addition, TG/DTA analysis (the result is shown in FIG. 6) was conducted and solid state $^{13}$C-NMR spectrum (the result is shown in FIG. 10) was also measured. In addition, the equivalents of hydrate were determined by direct titration of volumetric titration method of Karl-Fisher method.

Diffraction angles (2θ): 6.5, 11.7, 13.0, 14.0, 16.4, 18.6 and 21.6

Melting point: 174 to 178° C.

Reference Example 2

Figure 3:
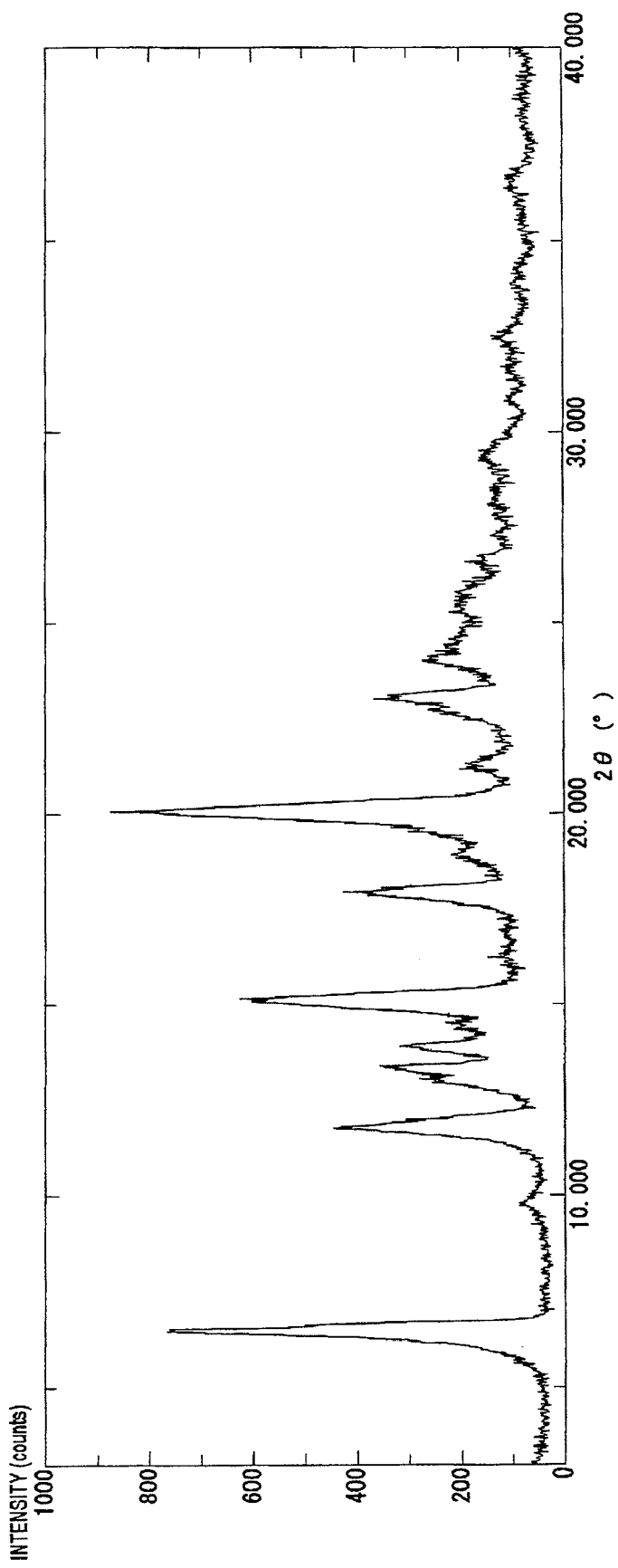
FIG. 3 shows powder X-ray diffraction diagram of crystalline form D obtained in Reference example 2. The axis of ordinate shows the intensity of X-rays, and the axis of abscissa shows the angle of the diffraction (2θ).
Figure 7:
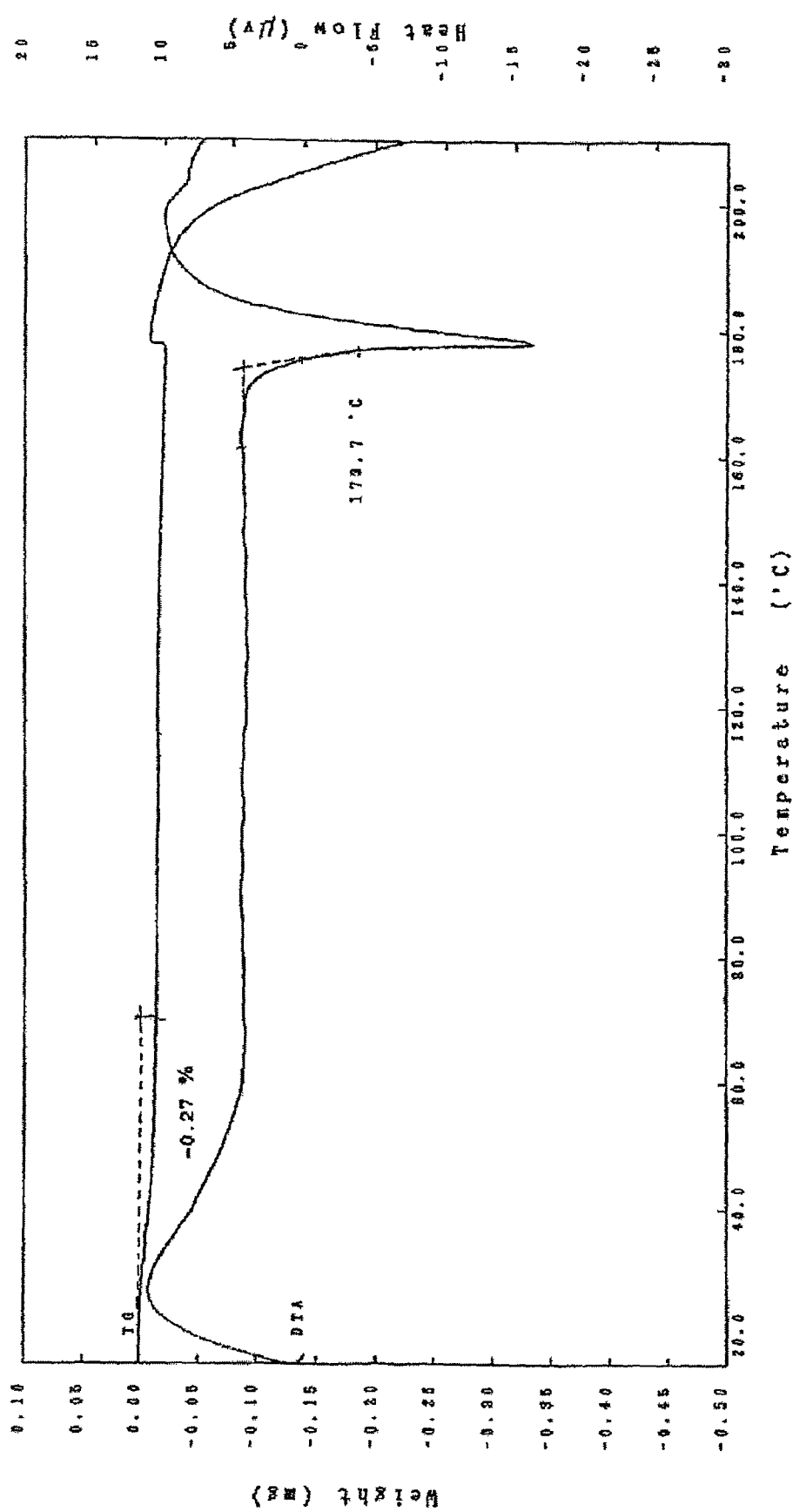
FIG. 7 shows TG/DTA data of crystalline form D obtained in Reference example 2 shown by the TG/DTA curves. The axis of ordinate shows the heat flow and weight, and the axis of abscissa shows the temperature.
Figure 11:
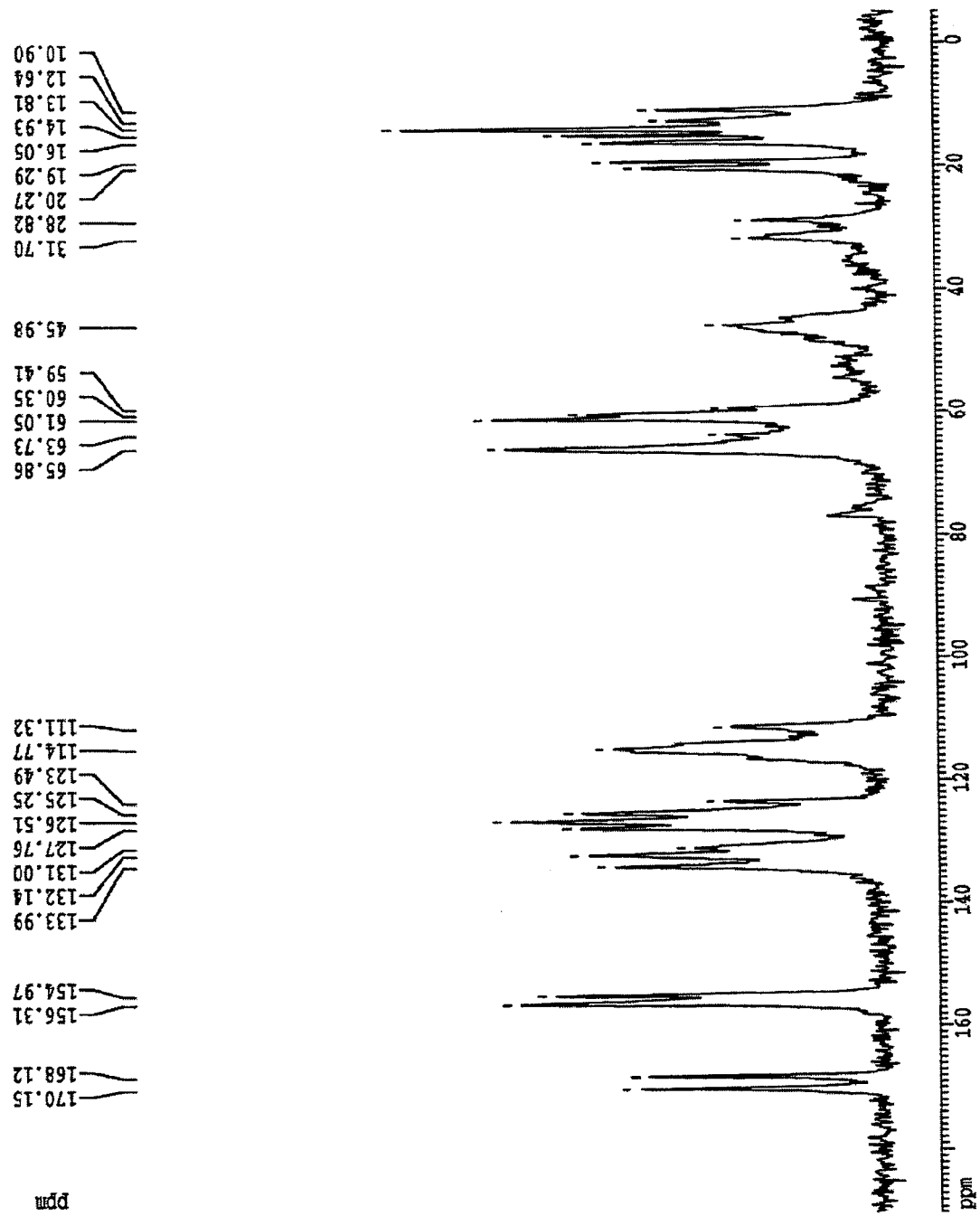
FIG. 11 shows solid state $C^{13}$-NMR spectrum of crystalline form D obtained in Reference example 2, the axis of abscissa shows the chemical shifts (ppm).

Crystalline form D of ethyl (−)-2-[4-[2-[[(1S,2R)-2-hydroxy-2-(4-hydroxyphenyl)-1-methylethyl]amino]ethyl]-2,5-dimethylphenoxy]-acetate hydrochloride Ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride ¼ hydrate (10 g) obtained in Reference example 1 was heated at 65° C. for 30 minutes, and the title crystals were obtained. The obtained crystals were measured by the powder X-ray diffraction analysis, and the result was shown in FIG. 3. In addition, TG/DTA analysis (the result is shown in FIG. 7) was conducted and solid state $^{13}$C-NMR spectrum (the result is shown in FIG. 11) was also measured.

Diffraction angles (2θ): 6.5, 11.8, 13.3, 15.1, 17.9 and 20.1

Melting point: 174 to 178° C.

Reference Example 3

Figure 4:
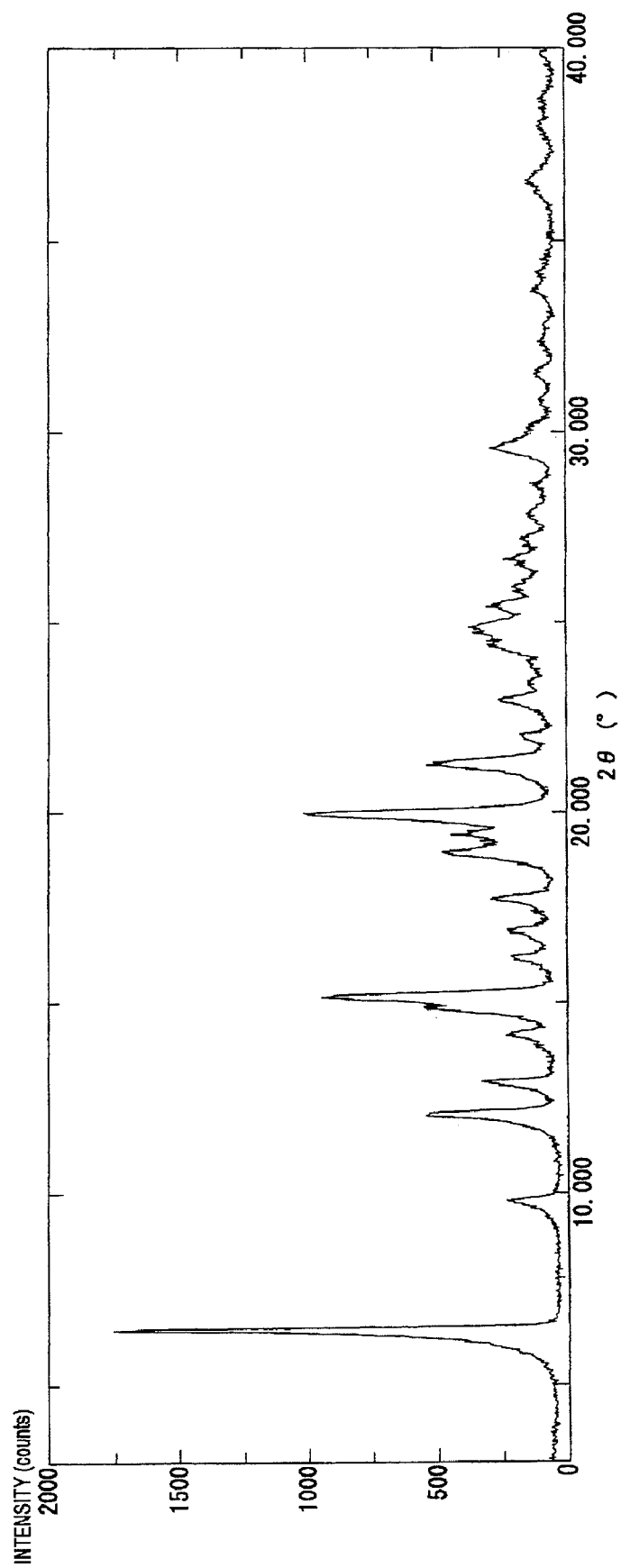
FIG. 4 shows powder X-ray diffraction diagram of crystalline form E obtained in Reference example 3. The axis of ordinate shows the intensity of X-rays, and the axis of abscissa shows the angle of the diffraction (2θ).
Figure 8:
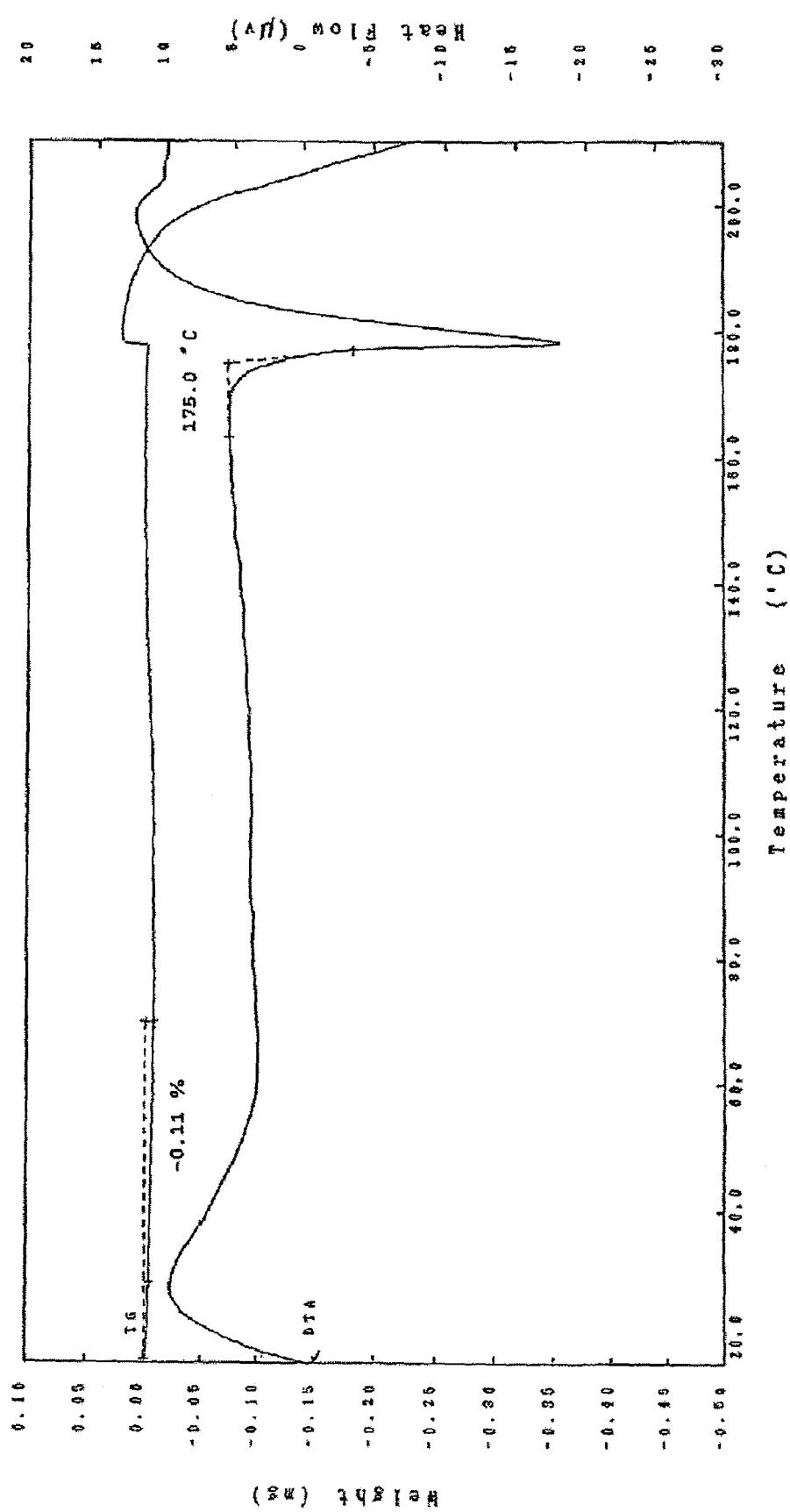
FIG. 8 shows TG/DTA data of crystalline form E obtained in Reference example 3 shown by the TG/DTA curves. The axis of ordinate shows the heat flow and weight, and the axis of abscissa shows the temperature.
Figure 12:
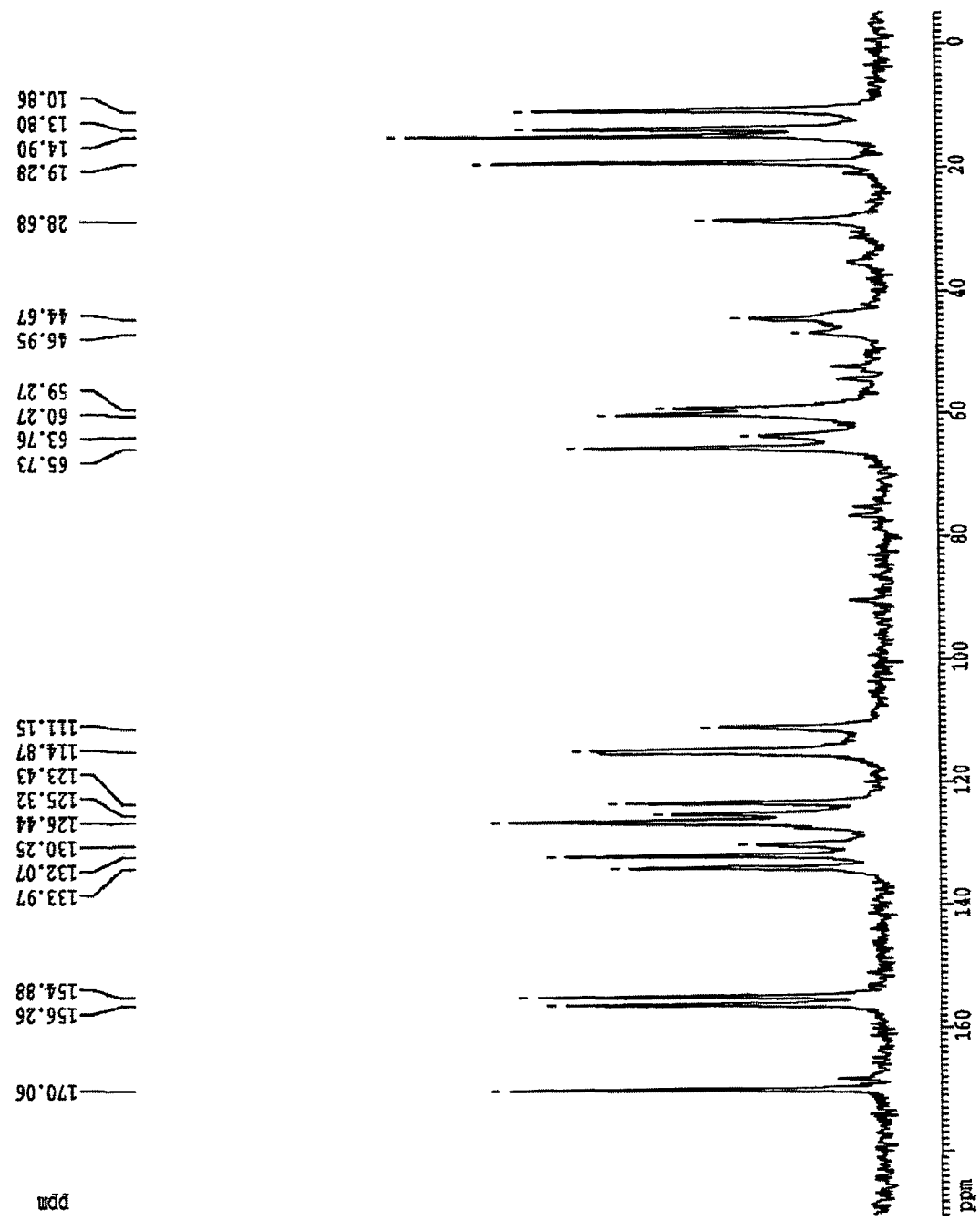
FIG. 12 shows solid state $C^{13}$-NMR spectrum of crystalline form E obtained in Reference example 3, the axis of abscissa shows the chemical shifts (ppm).

Crystalline form E of ethyl (−)-2-[4-[2-[[(1S,2R)-2-hydroxy-2-(4-hydroxyphenyl)-1-methylethyl]amino]ethyl]-2,5-dimethyl-phenoxy]acetate hydrochloride Ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride ¼ hydrate (10 g) obtained in Reference example 1 was heated at 120° C. for 15 minutes, and the title crystals were obtained. The obtained crystals were measured by the powder X-ray diffraction analysis, and the result is shown in FIG. 4. In addition, TG/DTA analysis (the result is shown in FIG. 8) was conducted and solid state $^{13}$C-NMR spectrum (the result is shown in FIG. 12) was also conducted.

Diffraction angles (2θ): 6.4, 9.8, 12.0, 15.1, 19.9 and 21.3

Melting point: 174 to 178° C.

Test Example 1

Stability Test 1 (60° C.)

After ethyl (−)-2-[4-[2-[[(1S,2R)-2-hydroxy-2-(4-hydroxyphenyl)-1-methylethyl]amino]ethyl]-2,5-dimethylphenoxy]-acetate hydrochloride obtained in Example 1 was stored at 60° C. for a week, chemical stability was determined by measuring the residual percentage of ethyl (−)-2-[4-[2-[[(1S,2R)-2-hydroxy-2-(4-hydroxylphenyl)-1-methylethyl]amino]ethyl]-2,5-dimethylphenoxy]acetate hydrochloride by HPLC and polymorphic stability was examined by the powder X-ray diffraction measurement. In addition, the change in appearance was also observed and the results are shown in Table 1.

The results are as shown in Table 1. on crystalline form C, the chemical purity was constant and polymorphic transformation did not occur. In addition, no change in appearance was observed and an excellent storage stability was shown.

TABLE 1

| crystal form | storage period | |
| --- | --- | --- |
| | at start crystal form C | after 1 week crystal form C |
| residual percentage (chemical purity %) | 99.6% | 99.6% |
| appearance | white | white |

Test Example 2

Stability Test 2 (140° C.)

After heating crystalline form C obtained in Example 1 to 140° C., change of the crystalline form was examined by the powder X-ray diffraction measurement. As a result, it was still crystalline form C even after heating at 140° C., and thus the stability of crystalline form C at a high temperature was confirmed.

INDUSTRIAL APPLICABILITY

This time, since crystalline forms C, D and E were newly found, they provided a new opportunity for the development of drug formulation whose performance characteristic is improved. Particularly, since crystalline form C has an excellent storage stability and stability against heat, it is suitable for formulation.

The invention claimed is:

1. Solid ethyl (−)-2-[4-[2-[[1S,2R]-2-hydroxy-2-(4-hydroxyphenyl)-1-methylethyl]amino]ethyl]-2,5-dimethylphenoxyacetate hydrochloride wherein the diffraction pattern by powder X-ray diffractometry has characteristic peaks at diffraction angles (2θ) of 9.0, 13.6, 18.7, 20.6 and 24.8.

2. A pharmaceutical composition comprising as an active ingredient a compound as claimed in claim 1.

3. An agent for treating pollakiuria or urinary incontinence comprising as an active ingredient a compound as claimed in claim 1.

* * * * *